United States Patent
Vilkov et al.

(10) Patent No.: US 9,952,179 B2
(45) Date of Patent: Apr. 24, 2018

(54) SYSTEM AND METHOD FOR TRACE DETECTION USING DUAL IONIZATION SOURCES

(71) Applicant: Rapsican Systems, Inc., Torrance, CA (US)

(72) Inventors: Andrey N. Vilkov, Aliso Viejo, CA (US); Jack A. Syage, Corona del Mar, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 14/666,856

(22) Filed: Mar. 24, 2015

(65) Prior Publication Data
US 2016/0282304 A1 Sep. 29, 2016
US 2017/0191962 A9 Jul. 6, 2017

(51) Int. Cl.
| | |
|---|---|
| H01J 27/00 | (2006.01) |
| G01N 27/62 | (2006.01) |
| H01J 37/08 | (2006.01) |
| H01J 49/10 | (2006.01) |
| G01N 33/22 | (2006.01) |
| G01N 33/00 | (2006.01) |

(52) U.S. Cl.
CPC ....... *G01N 27/622* (2013.01); *G01N 33/0036* (2013.01); *G01N 33/227* (2013.01); *H01J 37/08* (2013.01); *H01J 49/107* (2013.01)

(58) Field of Classification Search
None
See application file for complete search history.

(56) References Cited

U.S. PATENT DOCUMENTS

| | | | | |
|---|---|---|---|---|
| 6,630,664 B1* | 10/2003 | Syage | ............... | H01J 49/107 250/288 |
| 7,109,476 B2* | 9/2006 | Hanold | ............... | H01J 49/107 250/281 |
| 7,401,498 B2* | 7/2008 | Syage | ............... | G01N 27/626 73/28.01 |
| 2002/0179832 A1* | 12/2002 | Fischer | ............... | G01N 30/7253 250/288 |
| 2006/0255261 A1* | 11/2006 | Whitehouse | ............ | H01J 49/0431 250/288 |
| 2007/0176092 A1* | 8/2007 | Miller | ............... | G01N 27/624 250/288 |

(Continued)

OTHER PUBLICATIONS

Waltman, M.J.; "Atmospheric Pressure Chemical Ionization Sources used in the Detection of Explosives by Ion Mobility Spectrometry"; PNNL Report # 19261; U.S. Department of Energy; (2010); 98 pages.

*Primary Examiner* — Andrew Smyth
(74) *Attorney, Agent, or Firm* — Novel IP

(57) ABSTRACT

A dual source ionizer includes a first ionization source and a second ionization source. The first ionization source is configured to generate a first electric field. The first electric field has a first field strength that is insufficient to form $NO_x^-$ ions. The second ionization source is configured to generate a second electric field. The second electric field has a second field strength that is sufficient to form ozone and the $NO_x^-$ ions.

19 Claims, 5 Drawing Sheets

(56) References Cited

U.S. PATENT DOCUMENTS

2009/0134321 A1* 5/2009 Hoyes ................ C08L 23/04
250/282
2011/0186436 A1* 8/2011 Novosselov .......... B01D 15/08
204/600

* cited by examiner

SYSTEM AND METHOD FOR TRACE DETECTION USING DUAL IONIZATION SOURCES

BACKGROUND

The field of the disclosure relates generally to explosive trace detection (ETD) systems and, more particularly, to systems and methods for trace detection using dual ionization sources.

Various technologies exist for detection of substances of interest, such as explosives and illicit drugs. Some trace detection technologies use spectrometric analysis of ions formed by ionization of vapors of substances of interest. Spectrometric analysis includes ion mobility spectrometry and mass spectrometry, for example, both of which are common in trace detection.

Ionization is a process by which electrically neutral atoms or molecules acquire a negative or positive charge by gaining or losing electrons, by undergoing a reaction, or by combining with an adduct that imparts a positive or negative charge. The electrically charged atoms or molecules are referred to as ions. Ionization occurs when sufficiently energetic charged particles or radiant energy travel through gases. For example, ionization occurs when an electric current is passed through a gas, if the electrons constituting the current have sufficient energy to force other electrons from the neutral gas molecules. Ionization also occurs, for example, when alpha particles and electrons from radioactive materials travel through a gas. Numerous ionization sources are used today for a variety of purposes. Radioactive ionization sources are prevalent in ETD.

BRIEF DESCRIPTION

In one aspect, a dual source ionizer is provided. The dual source ionizer includes a first ionization source and a second ionization source. The first ionization source is configured to generate a first electric field. The first electric field has a first field strength that is insufficient to form $NO_x^-$ ions (nitrous oxide anions). The second ionization source is configured to generate a second electric field. The second electric field has a second field strength that is sufficient to form ozone and the $NO_x-$ ions.

In another aspect, a method of ionizing a gas is provided. The method includes ionizing the gas using a first ionization source. The first ionization source is configured to generate a low-strength electric field or no electric field. A second ionization source is then enabled for a duration. While enabled, the second ionization source ionizes the gas. The second ionization source is configured to generate a high-strength electric field.

In yet another aspect, a trace detection system is provided. The trace detection system includes a chamber, a first ionization source, a second ionization source, and a switch. The chamber is configured to contain a gas composed of at least vapor of a chemical substance sample. The first ionization source is configured to generate a low-strength electric field in the chamber to ionize the gas. The second ionization source is configured to generate a high-strength electric field in the chamber to ionize the gas. The switch is configured to enable the second ionization source for a portion of a scan duration. The switch is further configured to otherwise disable the second ionization source.

DRAWINGS

These and other features, aspects, and advantages of the present disclosure will become better understood when the following detailed description is read with reference to the accompanying drawings in which like characters represent like parts throughout the drawings, wherein.

Figure 1:
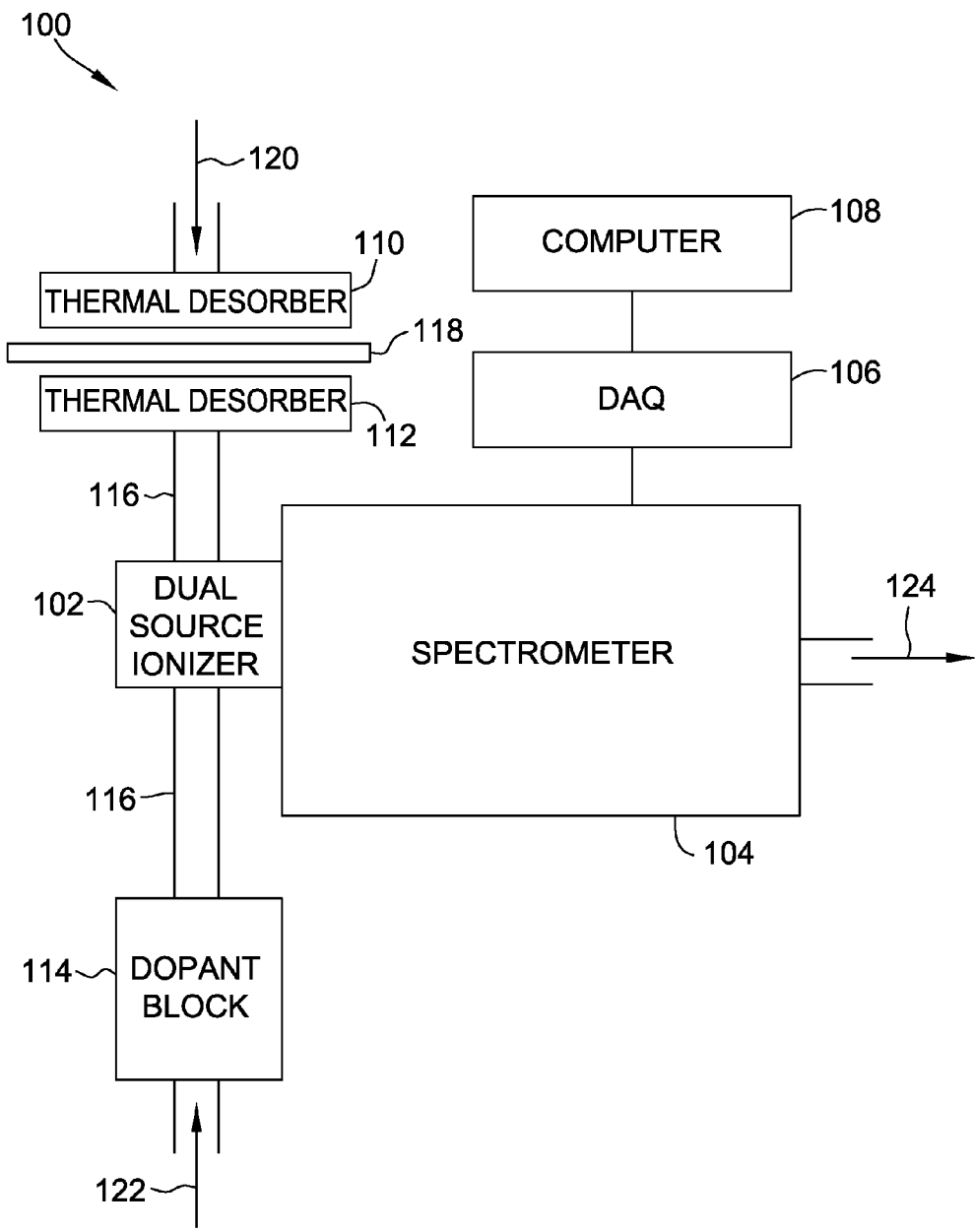
FIG. 1 is a block diagram of an exemplary trace detection system.

Unless otherwise indicated, the drawings provided herein are meant to illustrate features of embodiments of this disclosure. These features are believed to be applicable in a wide variety of systems comprising one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, a number of terms are referenced that have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged. Such ranges are identified and include all the sub-ranges contained therein unless context or language indicates otherwise.

During ionization in ambient atmospheric air, ionization sources typically produce significant amounts of ozone that leads to subsequent formation of $NO_x^-$ ions. The number of $NO_x^-$ ions formed from atmospheric air varies among ionization sources from high for electrical discharge ionization methods to low for photo-, x-ray, and radioactive sources. High amounts of ambient $NO_x^-$ ions may suppress the sensitivity of explosive trace detection (ETD) systems for nitrate-based explosives, including ammonium nitrate (AN) and urea nitrate (UN). For example, the atmospheric $NO_3^-$ ion overlaps in chemical composition with the nitrate $NO_3^-$ ion from nitrate-based explosives, decreasing the sensitivity for nitrate detection. The $NO_x^-$ ions are also helpful, as adduct ions, in detection of a variety of other explosives, including research department explosive (RDX), pentaerythritol tetranitrate (PETN), ethylene glycol dinitrate (EGDN), nitroglycerin (NG), Tetryl, and high melting explosive (HMX), among others. These other explosives are sometimes referred to as non-nitrate-based explosives. Nonnitrate-based explosives also include nitrate-containing compounds that are not detected by their respective nitrate ions. Detection of such explosives using $NO_3^-$ adduct ions can be very sensitive and selective, and is an inexpensive alternative for commonly used dopants, including chlorine-containing chemical substances.

In atmospheric air, $NO_x^-$ ions are formed by a series of chemical reactions referred to as pathways. The formation of ozone is a precursor to the formation of $NO_x^-$ ions. Ozone is formed readily by breaking molecular oxygen, $O_2$, into atomic oxygen, O, by radiation with an energy higher than the oxygen chemical bond, which is 5.15 electron volts (eV), according to a first pathway. The radiation may be electromagnetic, such as ultra-violet, X-ray, and gamma-ray, or particulate, such as alpha-particle and electron beams. An energy of 6.25 eV or higher is sufficient to excite ground state of nitrogen molecules $N_2$ to form the lowest $A^3\Sigma_u^+$ metastable state, which reacts with diatomic oxygen $O_2$ and then forms ozone, $O_3$, according to a second pathway.

In electrical discharge systems the production of ozone and $NO_x^-$ ions can be controlled through choice of conditions, such as flow rate and humidity. The production of $NO_x^-$ ions may also be controlled through use of ion suppressants. Use of these techniques in ETD systems makes the systems more complicated, less reliable, more costly, and heavy.

FIG. 1 is a block diagram of an exemplary trace detection system 100. Trace detection system 100 includes a dual source ionizer 102, a spectrometer 104, a data acquisition system (DAQ) 106, a computer 108, a thermal desorber that includes a first heating device 110, a second heating device 112, a dopant block 114, and ducts 116.

A sample swab 118, on which a chemical substance sample is present, is placed between first heating device 110 and second heating device 112. In alternative embodiments, the chemical substance sample may be introduced by any other suitable means, including direct intake of vapor of the chemical substance sample and any other device suitable for vaporizing the chemical substance sample. Air is drawn from a first air intake 120 over sample swab 118. Heat generated by first heating device 110 and second heating device 112 causes the chemical substance sample on sample swab 118 to vaporize and separate from sample swab 118. The air from first air intake 120 carries the vapor molecules through duct 116 into dual source ionizer 102. In alternative embodiments, first heating device 110 and second heating device 112 are replaced by another suitable device or method of vaporizing the chemical substance sample, including laser desorption, radio frequency heating, and microwave heating.

In certain embodiments, air is also drawn from a second air intake 122 across dopant block 114, releasing dopant and carrying it to dual source ionizer 102. Dopant present in dual source ionizer 102 alters electrochemical characteristics of the vapor molecules, which improves the efficiency of the ionization process.

Dual source ionizer 102 ionizes the vapor molecules, the ions of which are analyzed by spectrometer 104. Dual source ionizer 102 includes two sources within a chamber, which may include, for example, and without limitation, an electrical discharge ionization source, a photo-ionization source, an x-ray ionization source, or a radioactive ionization source. One of the two ionization sources generates a low-strength electric field or no electric field at all in the chamber. A low-strength electric field is one that is insufficient to supply enough energy to a liberated electron to break the chemical bonds of the oxygen molecules in the ambient air. The second of the two ionization sources generates a high-strength electric field. A high-strength electric field is one that is sufficient to supply enough energy to a liberated electron to break the chemical bonds of the oxygen molecules, which results in the formation of ozone and $NO_x^-$ ions. In one embodiment, for example, the first ionization source is a radioactive ionization source, and the second ionization source is an electrical discharge source. The definition of low-strength electric field and high-strength electric field, expressed in megavolts per meter (MV/m) varies with the pressure in the volume. As pressure is reduced, the necessary field strengths decrease.

Dual source ionizer 102 carries out ionization inside the chamber where the vapor molecules, dopants, and ambient air are present. In certain embodiments, each ionization source operates within its own, isolated volume within the chamber. In other embodiments, the two ionization sources operate within a single volume within the chamber.

Ionization is carried out over a scan duration. Within the scan duration, there is at least one period of time where $NO_x^-$ ions are not desirable for the purpose of trace detection, such as, for example, for detection of nitrate-based explosives. During this period, the second ionization source that generates the high-strength electric field is disabled, which inhibits the production of $NO_x^-$ ions. The first ionization source is enabled and ionizes the vapor molecules using a low-strength electric field or no electric field.

Also within the scan duration, there is at least one period of time where $NO_x^-$ ions are desirable for the purpose of trace detection, such as, for example, for detection of some explosives using $NO_x^-$ ions as adducts. During this period, the second ionization source is enabled and generates a high-strength electric field. The high-strength electric field ionizes the vapor molecules and results in formation of ozone and $NO_x^-$ ions. In certain embodiments, the second ionization source is enabled for multiple periods within the scan duration. In certain embodiments, the second ionization source is enabled for a single period. During this period, in certain embodiments, the first ionization source is disabled. In other embodiments, the first ionization source remains enabled while the second ionization source is enabled. In certain embodiments, the enabling and disabling of the first and second ionization sources are controlled by a pulse signal, such as a square wave, controlling a switch.

Spectrometer 104 carries out spectrometry to screen the chemical substance for certain target chemical substances, such as, for example, explosives and drugs. Spectrometer 104 may be, for example, a mass spectrometer or an ion mobility spectrometer. Results of the spectrometry carried out by spectrometer 104 on the ions are collected by DAQ 106 and disseminated to computer 108, where a detection or a failure to detect is indicated.

Some embodiments involve the use of one or more electronic or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

Figure 2:
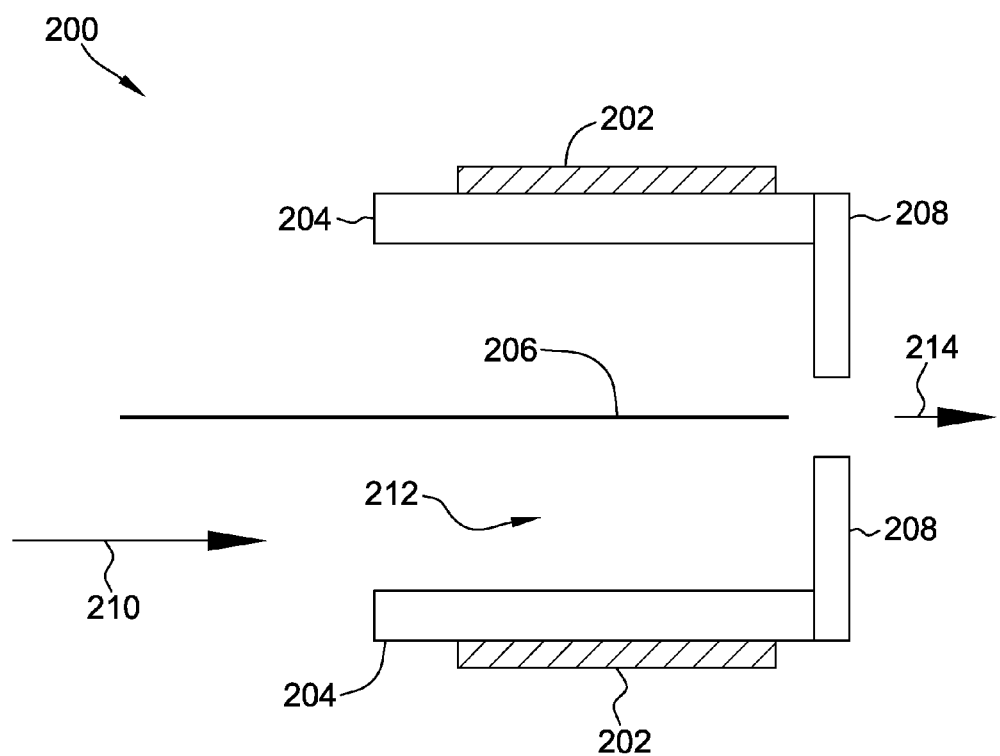
FIG. 2 is a diagram of an exemplary dual source ionizer for use in the trace detection system shown in FIG. 1.

FIG. 2 is a diagram of an exemplary dual source ionizer 200 for use in trace detection system 100 (shown in FIG. 1). Dual source ionizer 200 includes a radioactive foil 202 around a cylindrical foil holder 204. Radioactive foil 202 is a first ionization source. Dual source ionizer 200 also includes a corona needle 206 and an aperture plate 208, which form a second ionization source.

During operation, gases 210 enter a volume 212 at least partially defined by cylindrical foil holder 204 and aperture plate 208. The gases are ionized, and ions 214 leave volume 212. Ionization is carried out over a period of time referred to as a scan duration. The scan duration is based on the time required for target chemical substances to separate from sample swab 118 and vaporize as sample swab 118 is heated. Radioactive foil 202 generates a low-strength electrical field in volume 212 and, more specifically, no field at all. Ionization is carried out by radioactive radiation rather than an electric field. Consequently, radioactive foil 202 does not generate significant amounts of ozone or $NO_x^-$ ions during ionization. In contrast, corona needle 206 and aperture plate 208 are an electrical discharge ionization source, which can generate various strength electric fields. Corona needle 206 generates a high-strength electric field, one that is sufficient to liberate free electrons from the gas molecules and transfer sufficient kinetic energy to the free electrons to break the chemical bonds in the oxygen molecules of air, or to form the metastable state $N_2^*(A^3\Sigma_u^+)$ of molecular nitrogen and, subsequently, molecules of ozone. For example, at normal atmospheric pressure, or roughly 1 atmosphere, an electric field having a strength of 12.5 MV/m or more will cause formation of the metastable state $N_2^*(A^3\Sigma_u^+)$ of molecular nitrogen and, subsequently, molecules of ozone. Conversely, at 1 atmosphere, an electric field having a strength of 10 MV/m or less is insufficient for a liberated electron to acquire the necessary kinetic energy at the time of collision with a molecule to break the oxygen bonds. As pressure is reduced, in alternative embodiments, the strength of the electric field required to break the oxygen bonds also decreases, due to the inverse relationship between pressure and the average distance between collisions of electrons with molecules. For example, an ionization source operating in a volume having a pressure between 0.1 Torr and 100 Torr requires a lower strength electric field to break the oxygen bonds than a volume at a pressure between 100 Torr and 1 atmosphere. Normal atmospheric pressure is substantially 1 atmosphere. The typical range of normal atmospheric pressure is from 0.80 to 1.05 atmosphere. In certain embodiments, for example, the ionization source operates in a volume having a pressure near zero atmosphere. In other embodiments, for example, the ionization source operates in a volume having pressure up to 10 atmosphere.

Figure 3:
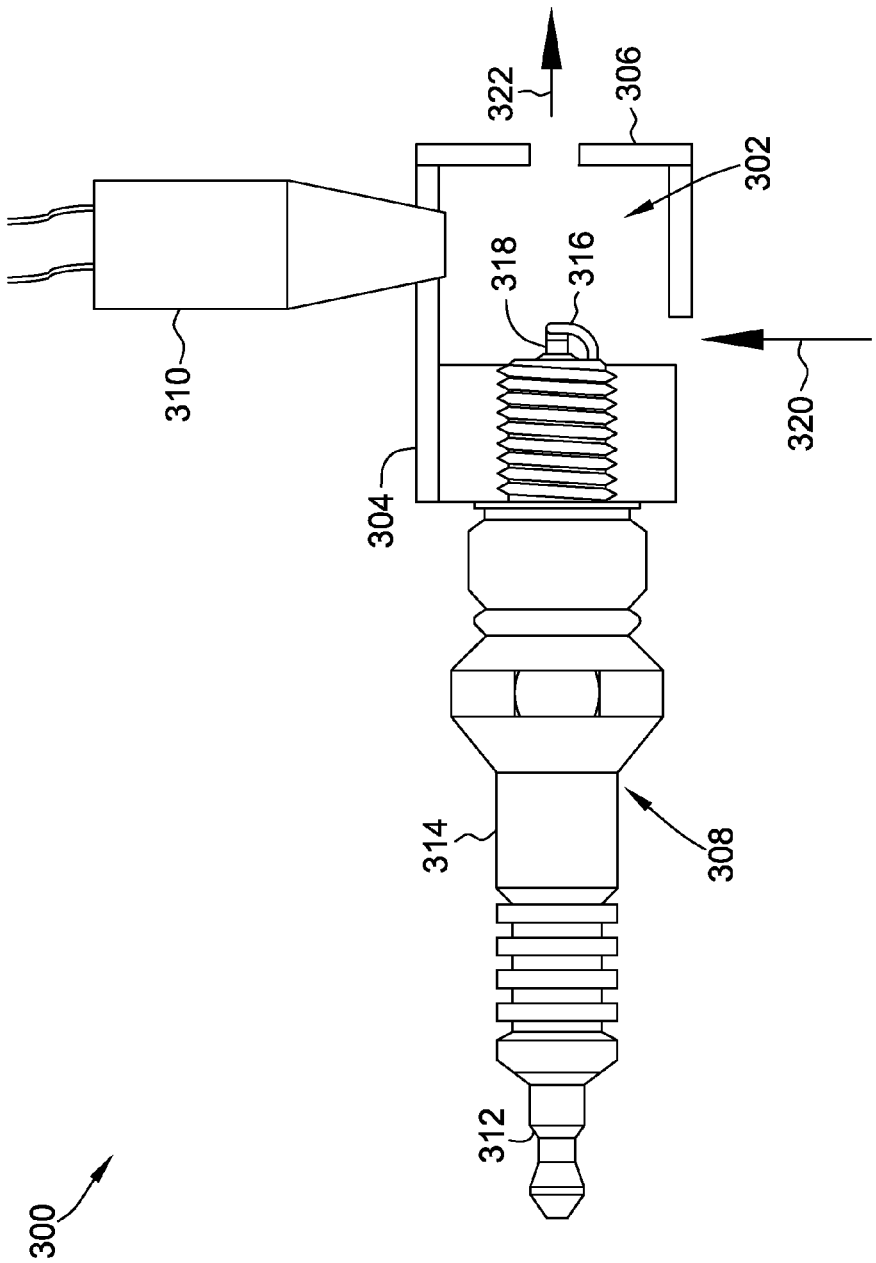
FIG. 3 is a diagram of another exemplary dual source ionizer for use in the trace detection system shown in FIG. 1.

FIG. 3 is a diagram of another exemplary dual source ionizer 300 for use in trace detection system 100 (shown in FIG. 1). Dual source ionizer 300 includes a volume 302 at least partially defined by a housing 304 and an aperture plate 306, an electrical discharge source 308, and an X-ray source 310. Electrical discharge source 308 includes a connector 312, an insulator 314, a ground electrode 316, and a high-voltage electrode 318.

During operation, gases 320 enter volume 302. X-ray source 310 generates a low-strength electric field that ionizes gases 320 within volume 302 over a scan duration. Electrical discharge source 308 produces a high-strength electric field within volume 302 by energizing high-voltage electrode 318. The high-strength electric field ionizes gases 320 and produces ions 322 of gases 320, as well as ozone and $NO_x^-$ ions.

Figure 4:
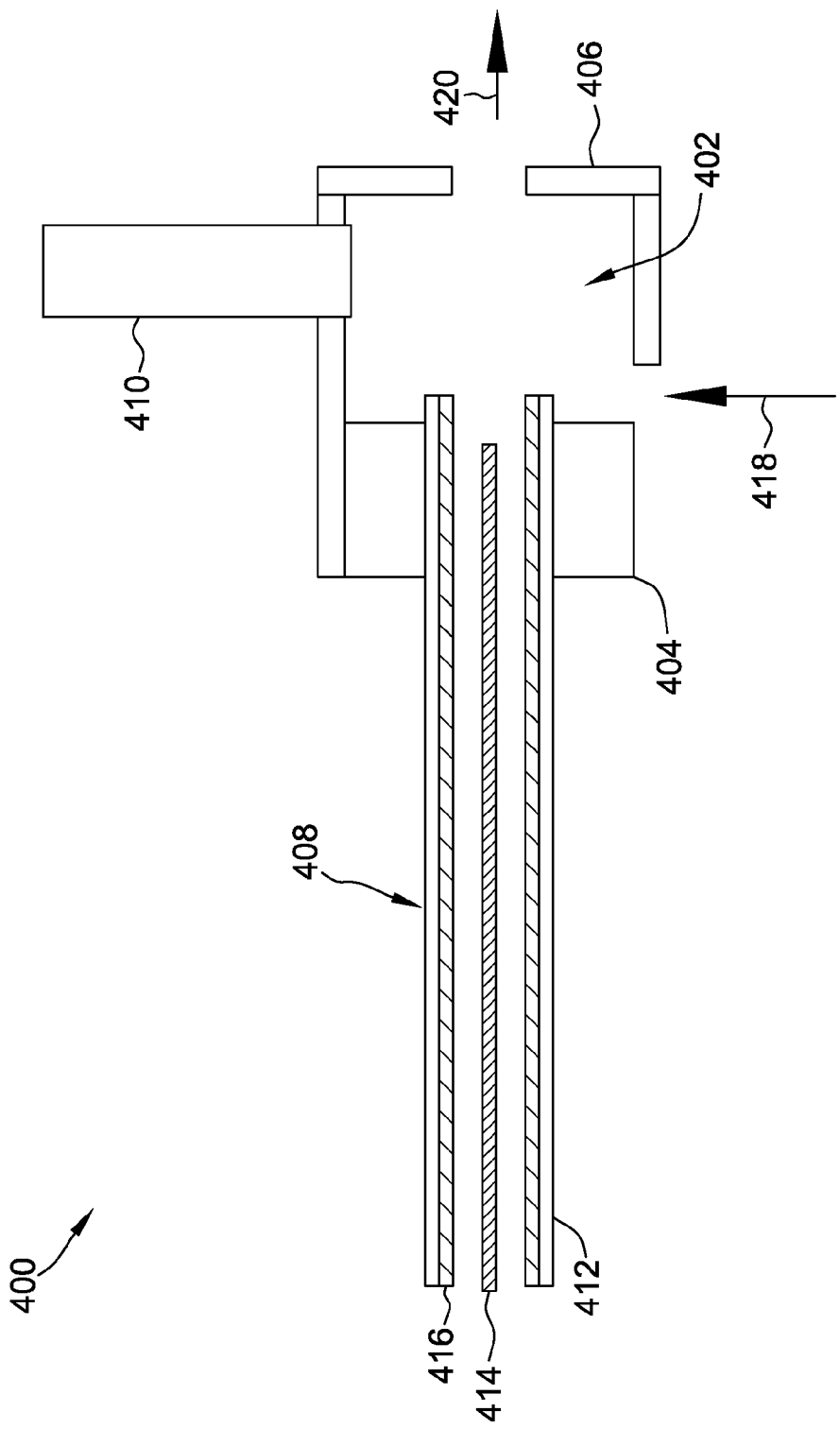
FIG. 4 is a diagram of yet another exemplary dual source ionizer for use in the trace detection system shown in FIG. 1.

FIG. 4 is a diagram of yet another exemplary dual source ionizer 400 for use in trace detection system 100 (shown in FIG. 1). Dual source ionizer 400 includes a volume 402 at least partially defined by a housing 404 and an aperture plate 406, an electrical discharge source 408, and an ultraviolet (UV) lamp 410, such as a krypton lamp. Electrical discharge source 408 includes an outer electrode 412 separated from an inner electrode 414 by a dielectric insulator 416.

During operation, gases 418 enter volume 402 and ions 420 exit. UV lamp 410 ionizes molecules of gases 418 without generating an electric field. Electrical discharge source 408 produces a high-strength electric field between outer electrode 412 and inner electrode 414. While UV lamp 410 is enabled and electrical discharge source 408 is disabled, the electric field within volume 402 is insufficient to generate ozone and $NO_x^-$ ions. When enabled, electrical discharge source 408 causes formation of ozone and $NO_x^-$ ions.

Figure 5:
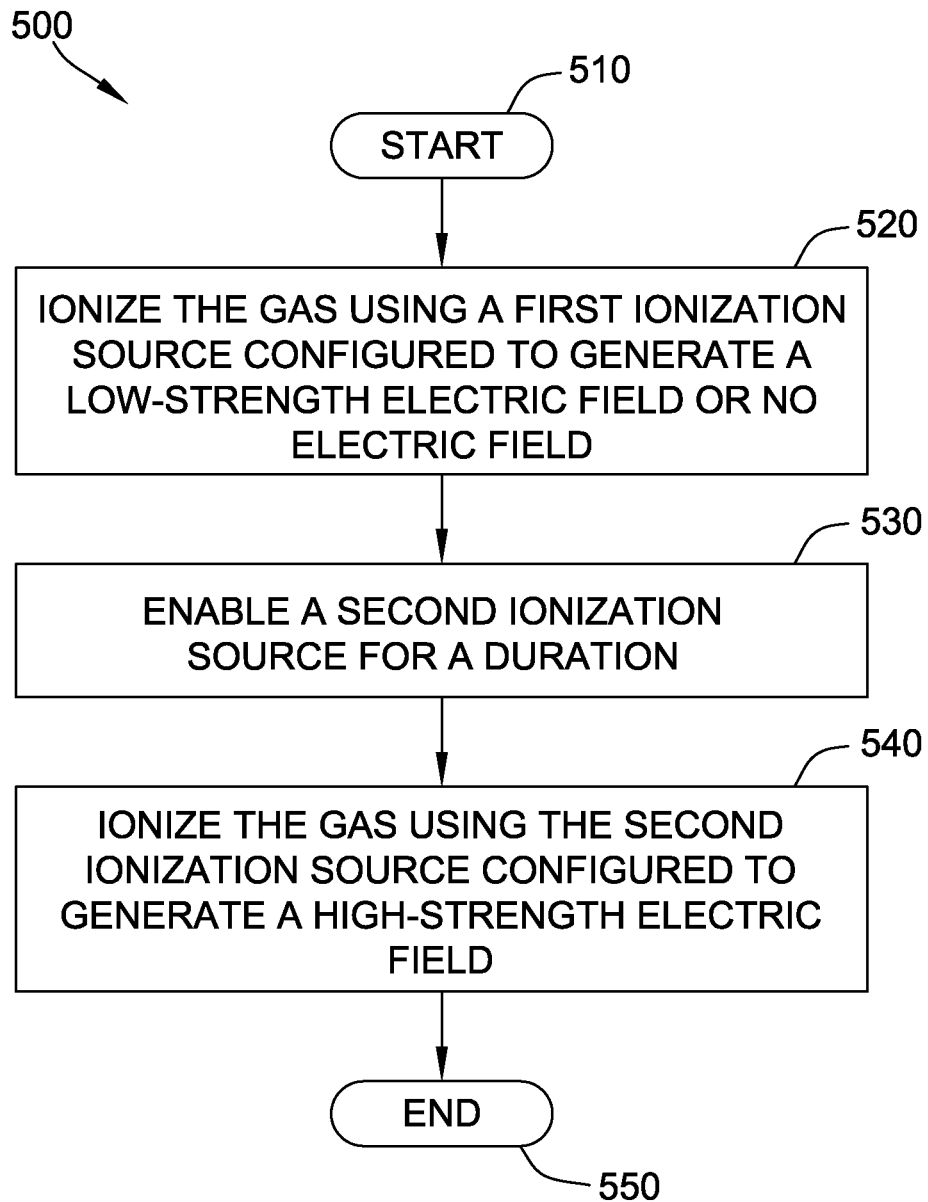
FIG. 5 is a flow diagram of an exemplary method of ionizing gas.

FIG. 5 is a flow diagram of an exemplary method 500 of ionizing a gas. At a first ionization step 520, the gas is ionized using a first ionization source. The first ionization source generates a low-strength electric field or no electric field. The low-strength electric field, or no electric field at all, is insufficient to cause liberated free electrons to gain enough energy to break the chemical bonds in oxygen molecules, and thus will not contribute to the formation of ozone and $NO_x^-$ ions.

At a switching step 530, a second ionization source is enabled for a duration. For trace detection systems, the duration is determined as a function of the target chemical substance. The duration is a portion of a longer scan duration. The first ionization source can be enabled or disabled while the second ionization source is enabled. In certain embodiments, the first ionization source is enabled for the full scan duration, and the second ionization source is enabled only for the shorter duration. In certain embodiments, the first ionization source and second ionization source are alternately enabled.

While the second ionization source is enabled for the duration, at a second ionization step 540, the gas is ionized by the second ionization source. The second ionization source generates a high-strength electric field. The high-strength electric field is sufficient for liberated free electrons to gain enough energy to break the chemical bonds of oxygen molecules, resulting in the formation of ozone and $NO_x^-$ ions, in addition to ions of the gas. The method ends at an end step 550.

An exemplary technical effect of the methods, systems, and apparatus described herein includes at least one of: (a) detection of wide variety of chemical substances, including various explosives; (b) detection of nitrate-based chemical substances, including nitrate-based explosives; (c) improved sensitivity to nitrate-based explosives; (d) improved detection of some explosives using $NO_3^-$ adduct ions; (e) reduced complexity in explosive trace detection systems fielded for detecting nitrate-based, such as AN and UN, and non-nitrate-based explosives, such RDX, PETN, EGDN, NG, Tetryl, HMX, and certain nitrate-containing compounds that are not detected by their respective nitrate ions, among others; and (f) improved weight, cost, and reliability due to reduced complexity of explosive trace detection systems.

Exemplary embodiments of methods, systems, and apparatus for dual source ionizers are not limited to the specific embodiments described herein, but rather, components of systems and/or steps of the methods may be utilized independently and separately from other components and/or steps described herein. For example, the methods may also be used in combination with other non-conventional dual source ionizer, and are not limited to practice with only the systems and methods as described herein. Rather, the exemplary embodiment can be implemented and utilized in connection with many other applications, equipment, and systems that may benefit from increased efficiency, reduced operational cost, and reduced capital expenditure.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A dual source ionizer comprising:
  a first ionization source configured to generate a first electric field, the first electric field having a first field strength insufficient to form $NO_x^-$ ions;
  a second ionization source configured to generate a second electric field, the second electric field having a second field strength sufficient to form ozone and $NO_x^-$ ions; and
  a controller configured to disable said second ionization source for a period of time while said first ionization source is enabled to screen a chemical substance for a target nitrate-based chemical substance using the first electric field.

2. The dual source ionizer of claim 1 wherein said first ionization source comprises a radioactive ionization source.

3. The dual source ionizer of claim 1 wherein the first ionization source comprises a photoionization source.

4. The dual source ionizer of claim 1 wherein the second ionization source comprises an electrical discharge radiation source.

5. The dual source ionizer of claim 1 wherein the second field strength is at least 12.5 megavolts per meter, and wherein the second electric field is generated in a volume having a pressure of substantially 1 atmosphere.

6. A method of ionizing a gas, the method comprising:
  ionizing the gas during a first period of time of a scan duration using a first ionization source configured to generate one of the group consisting of a low-strength electric field and no electric field;
  disabling a second ionization source during the first period of time for screening ions of the gas for a nitrate-based chemical substance, the second ionization source configured to generate a high-strength electric field; and
  ionizing the gas during a second period of time of the scan duration using the second ionization source to screen the gas for a non-nitrate-based chemical substance.

7. The method of claim 6, wherein the scan duration is determined according to a vaporization time of a chemical substance sample from which the gas is formed.

8. The method of claim 6 further comprising disabling the first ionization source before ionizing the gas using the second ionization source.

9. The method of claim 6 further comprising performing spectrometry on ions of the gas to screen for a target chemical substance.

10. The method of claim 9, wherein performing spectrometry comprises performing mass spectrometry.

11. The method of claim 9, wherein performing spectrometry further comprises screening for a nitrate-based explosive and for a non-nitrate-based explosive.

12. A trace detection system comprising:
  a chamber configured to contain a gas composed of at least vapor of a chemical substance sample;
  a first ionization source configured to generate a low-strength electric field in said chamber to ionize the gas;
  a second ionization source configured to generate a high-strength electric field in said chamber to ionize the gas; and
  a controller configured to:
    enable said first ionization source and disable said second ionization source during a first period of time of a scan duration to screen the gas for a target nitrate-based chemical substance, and
    enable said second ionization source during a second period of time of the scan duration to screen the gas for a target non-nitrate-based chemical substance.

13. The trace detection system of claim 12 further comprising a spectrometer configured to screen ions of the gas for a nitrate-based explosive and for non-nitrate-based explosives.

14. The trace detection system of claim 13, wherein said chamber comprises a first volume within which said first ionization source operates, and a second volume, distinct from said first volume, within which said second ionization source operates.

15. The trace detection system of claim 14, wherein said spectrometer is further configured to screen ions from said first volume for the nitrate-based explosives, and to screen ions from said second volume for the non-nitrate-based explosives.

16. The trace detection system of claim 12, wherein said low-strength electric field is configured to:
  liberate a free electron from a molecule of the gas; and
  accelerate the free electron to a first kinetic energy level, the first kinetic energy level insufficient to break chemical bonds of diatomic oxygen.

17. The trace detection system of claim 12, wherein said high-strength electric field is configured to:
  liberate a free electron from a molecule of the gas; and
  accelerate the free electron to a second kinetic energy level, the second kinetic energy level sufficient to form metastable nitrogen molecules.

18. The dual source ionizer of claim 1 wherein the first ionization source comprises an X-ray source.

19. The dual source ionizer of claim 1 wherein the first field strength is no greater than 10 megavolts per meter, and wherein the first electric field is generated in a volume having a pressure of substantially 1 atmosphere.

* * * * *